United States Patent [19]
Nakamura et al.

[11] Patent Number: 5,078,987
[45] Date of Patent: Jan. 7, 1992

[54] IODINE MICROBICIDE COMPOSITION

[75] Inventors: Yoshiaki Nakamura; Ryoichi Fujibayashi; Yuji Murakami, all of Osaka, Japan

[73] Assignee: Sunstar K.K., Osaka, Japan

[21] Appl. No.: 549,795

[22] Filed: Jul. 9, 1990

Related U.S. Application Data

[62] Division of Ser. No. 268,411, Nov. 8, 1988, Pat. No. 4,985,234.

[30] Foreign Application Priority Data

May 20, 1988 [JP] Japan .................. 63-124183

[51] Int. Cl.$^5$ .................................................. A61L 1/04
[52] U.S. Cl. ....................................... 424/43; 424/47; 424/45; 424/78.25; 222/394; 222/402.1; 222/402.13
[58] Field of Search .................. 424/43, 45, 47, 78, 424/80; 222/394, 402.1, 402.13

[56] References Cited
U.S. PATENT DOCUMENTS

| | | |
|---|---|---|
| 3,185,350 | 5/1965 | Abplanalp et al. ............ 222/402.11 |
| 3,260,416 | 7/1966 | Ablanalp ........................ 222/402.13 |
| 4,478,853 | 10/1984 | Chaussee .................... 424/47 |
| 4,500,339 | 2/1985 | Young et al. .................. 424/78 |
| 4,548,807 | 10/1985 | Westfall et al. ................ 424/45 |
| 4,716,032 | 12/1987 | Westfall et al. ................ 424/45 |
| 4,985,234 | 1/1991 | Nakamura et al. ............. 424/45 |

Primary Examiner—Thurman K. Page
Assistant Examiner—Donald R. McPhail
Attorney, Agent, or Firm—Sughrue, Mion, Zinn, Macpeak & Seas

[57] ABSTRACT

A substantially non-aqueous iodine microbicide composition comprising (a) a povidone-iodine in an amount of from 0.0005% to 1.0% by weight based on the total amount of the composition, and (b) a solvent comprising a lower alcohol having from 1 to 3 carbon atoms or a mixture of a lower alcohol having from 1 to 3 carbon atoms and a non-hydrated polyhydric alcohol, and an aerosol-type iodine microbicide composition containing the iodine microbicide composition.

4 Claims, 3 Drawing Sheets

IODINE MICROBICIDE COMPOSITION

This is a divisional of application Ser. No. 07/268,411 filed Nov. 8, 1988, U.S. Pat. No. 4,985,234.

FIELD OF THE INVENTION

The present invention relates to a substantially non-aqueous iodine microbicide composition and, more precisely, to a substantially non-aqueous iodine microbicide composition which is excellent in the storage stability for a long period of time even when concentration of the iodine in the composition is low.

BACKGROUND OF THE INVENTION

Iodine has a high microbicidal activity and has an extremely low toxicity to human bodies, and therefore it is widely utilized as a component for microbicides.

As a solvent for such iodine microbicide composition, an aqueous solution is generally utilized, but iodine is hardly stable in an aqueous solution. Accordingly, when an iodine-containing aqueous solution is stored for a long period of time, iodine therein would decompose and the iodine concentration in the resulting solution would decrease.

This phenomenon is more remarkable when the iodine concentration in the solution is lower. Accordingly, in order to inhibit the decrease of the iodine content in a conventional iodine microbicide composition of an aqueous solution system, the iodine concentration in the aqueous solution should be made higher, being 0.5% or more, so as to maintain the stability of the aqueous solution.

However, it is known that the microbicidal activity of iodine becomes maximum when the concentration of the free active iodine (hereinafter referred to as "effective iodine concentration") is in the range of from 10 to 100 ppm, and therefore, if the iodine content is 0.5% or more, the concentration is too high to sufficiently display the microbicidal power. This is a problem. In fact, the effective iodine concentration of conventional iodine microbicide compositions is almost from about 6,000 to 17,000 ppm and, therefore, the microbicidal effect of such compositions is sacrificed for the stability of the iodine content therein.

In addition, if the iodine concentration is to high, there is another problem that the offensive odor is too strong and the substances to be protected from microbes by the microbicide would disadvantageously be colored.

Under these circumstances, it has been desired to develop an iodine microbicide composition having a low iodine concentration and having a high storage stability.

Japanese Patent Publication No. 2242/88 (corresponding to U.S. Pat. No. 4,271,149) illustrates an iodine microbicide composition with a low iodine concentration which, however, essentially uses an aqueous solution as a solvent, similar to the above-mentioned conventional microbicide, and, therefore, the microbicidal power of the composition could not be sufficient.

U.S. Pat. No. 4,151,275 teaches the use of a solvent containing an alcohol in a high concentration for an iodine composition having a high iodine concentration of from 1.8 to 2.2 g/100 ml. With this composition, however, none of the above-mentioned problems of the deterioration of the microbicidal activity because of the high iodine concentration, the unpleasant feeling because of the offensive odor and the coloration of the substances to be protected from microbes could be overcome.

In actual use, the conventional high iodine microbicidal compositions have various problems such that these must be diluted just before use and the dilution requires complicated operation and, therefore, construction articles, such as a stool, etc., could not be disinfected with ease.

Another means of spraying an iodine microbicide from an aerosol container containing the microbicide has been proposed. Such means is advantageous since these do not require dilution of the microbicide and the aerosol container can be used with ease. However, conventional aerosol containers contain metallic parts everywhere because of the gaseous pressure-resistance, and the metallic parts would be corroded by the metal-corroding action of the iodine microbicide in the container or the metallic parts would often have an influence on the stability of iodine in the microbicide to decrease the effective iodine concentration. Accordingly, it is unsuitable to put an iodine microbicide in an aerosol container with metallic parts.

It may be considered to form an aerosol container from a synthetic resin, but synthetic resins generally have a large iodine gas permeability. Therefore, if an iodine microbicide is filled in a synthetic resin container, the iodine would permeate through the container and diffuse out therefrom. Thus, it is also unsuitable to put an iodine microbicide in an aerosol container made of a synthetic resin.

SUMMARY OF THE INVENTION

An object of the present invention is to provide an iodine microbicide composition excellent in both microbicidal power and long-term storage stability.

Another object of the present invention is to provide an aerosol-type iodine microbicide composition which can be used with ease and is excellent in both microbicidal power and long-term storage stability.

The above and other objects and effects of the present invention will be apparent from the following description.

The present inventors have found that the above objects of the present invention can be attained by a substantially non-aqueous iodine microbicide composition comprising (a) a povidone-iodine in an amount of from 0.0005% to 1.0% by weight based on the total amount of the composition, and (b) a solvent comprising a lower alcohol having from 1 to 3 carbon atoms or a mixture of a lower alcohol having from 1 to 3 carbon atoms and a non-hydrated polyhydric alcohol, and an aerosol-type iodine microbicide composition comprising an aerosol container having contained therein the above iodine microbicide composition and a propellant, the aerosol container comprising a tank body, a mountain cap, a housing and a stem which are made of one or more synthetic resins selected from the group consisting of a polyacrylonitrile resin, a polyethylene terephthalate resin and a polyoxymethylene resin.

DETAILED EXPLANATION OF THE INVENTION

Figure 1:
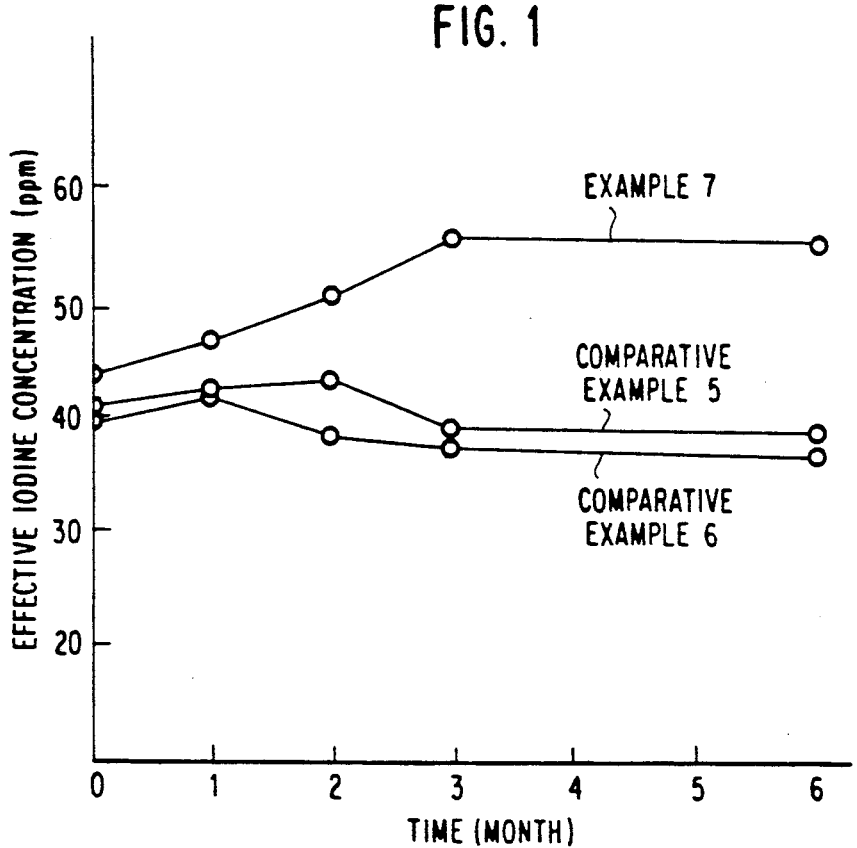
FIG. 1 is a graph showing the time-dependent change of the effective iodine concentration in the iodine microbicide compositions prepared in Example 7 and Comparative Examples 5 and 6 each having a different ethanol concentration, the compositions being stored under the condition of $-5°$ C.

The present inventors variously studied so as to overcome the prior art problems and have unexpectedly found that the incorporation of a particular lower alcohol or a combination of a particular lower alcohol and a non-hydrated polyhydric alcohol into a particular amount of povidone-iodine is effective for stable storage of the resulting composition for a long period of time even when the iodine concentration in the composition is low. Accordingly, all the problems in the conventional high iodine compositions, which include the deterioration of the microbicidal activity because of the high iodine concentration, the unpleasant feeling because of the offensive odor and the coloration of the substances to be protected from microbes with the composition, could be overcome.

Further, the composition of the present invention may be put in a container made of a particular synthetic resin to give a convenient aerosol-type iodine microbicide composition, in which the diffusion of iodine from the container may be prevented and the reaction between iodine and the container to cause the deterioration of the two may also be prevented. On the basis of the said discovery, the present invention which will be illustrated in detail hereinafter has been completed.

As the povidone-iodine for use in the composition of the present invention, various commercially available products may be used, for example, PVP-IODINE 30/60 (manufactured by BASF), PVP-Iodine 10 (manufactured by GAF), etc. The povidone-iodine is incorporated into the composition in a proportion of from 0.0005% by weight (corresponding to an effective iodine concentration of 0.5 ppm) to 1.0% by weight (corresponding to an effective iodine concentration of 1,000 ppm), preferably from 0.01% by weight (corresponding to an effective iodine concentration of 10 ppm) to 0.5% by weight (corresponding to an effective iodine concentration of 500 ppm), based on the total weight of the composition. If the amount is less than 0.0005% by weight, the microbicidal effect would be insufficient and the stability of the povidone-iodine could not be maintained. If the amount is more than 1.0% by weight, the offensive odor would become unpleasantly too strong and, in addition, when the composition is applied to a substance to be protected from microbes, the substance would be inconveniently colored or the appearance of the color of the substance itself would often be too much strengthened because of the application of the composition thereto so that the commercial value of the substance would be reduced.

Examples of the lower alcohol having from 1 to 3 carbon atoms used in the composition of the present invention include methanol, ethanol, n-propanol, isopropanol, etc. These can be used singly or in combination of two or more of them, preferably in an amount of 80% by weight or more based on the total amount of the composition.

In accordance with the present invention, a non-hydrated polyhydric alcohol can be used as the solvent together with the lower alcohol having from 1 to 3 carbon atoms, examples of which include ethylene glycol, propylene glycol, polyethylene glycol, polypropylene glycol, glycerin, etc. These can be used singly or in combination of two or more of them.

The solvent can be used in the form of a single system comprising lower alcohol(s) only or in the form of a mixed system comprising lower alcohol(s) and non-hydrated polyhydric alcohol(s) as blended in any desired proportion. However, from the viewpoint of strengthening the microbicidal activity of the composition, it is preferred to use a solvent comprising lower alcohol(s) only but containing no polyhydric alcohol.

When the iodine microbicide composition is put in an aerosol container made of a particular material to give an aerosol-type microbicidal composition which is then applied to stools, garbage boxes, etc., it is also preferred that polyhydric alcohols are not used as the solvent since these are poor in the drying property. On the other hand, when their composition is applied to human bodies, it is often preferred to use polyhydric alcohol(s) together with the lower alcohol(s) in view of the moisture-keeping effect for the skin. When the lower alcohol(s) only is(are) used, it is preferred that the amount of methanol and propanol is smaller than that of ethanol since the former have problems with toxicity and odor. More preferably, ethanol only is used as the lower alcohol.

The solvent for use in the composition of the present invention is required to be substantially non-aqueous for the purpose of stabilizing the iodine in the composition for a long period of time. The term "substantially non-aqueous" herein means that water is not intended to be positively incorporated into the composition as one constitutional component but the water, if any, as inevitably contained in the lower alcohol or the like as a solvent for the composition is not intended to be excluded.

The iodine microbicide composition of the present invention may optionally contain any other additives such as a surfactant, an organic acid, a deodorizer, a perfume and the like, if desired, provided that the additives do not have a bad influence on the resulting composition.

The aerosol-type iodine microbicide composition of the present invention is formed by putting the above-mentioned iodine microbicide composition, which is not diluted, in an aerosol container which can house the iodine microbicide composition while keeping the chemical property thereof stable. Specifically, the aerosol container for use in the present invention comprises the main constitutional parts of a tank body, a mountain cap, a housing, a guide screw, a stem, a push button, a dip tube, a spring and a gasket, and at least the tank body, the mountain cap, the housing and the stem are made of one or more synthetic resins having a small gas-permeability to iodine. The above-mentioned iodine microbicidal composition of the present invention is put into the aerosol container together with a propellent such as a Freon gas, a liquefied petroleum gas, dimethyl ether, carbon dioxide gas, or the like, to give an aerosol-type iodine microbicide composition according to the present invention.

One embodiment of the aerosol-type iodine microbicide composition is explained with reference to the drawing attached hereto.

Figure 4:
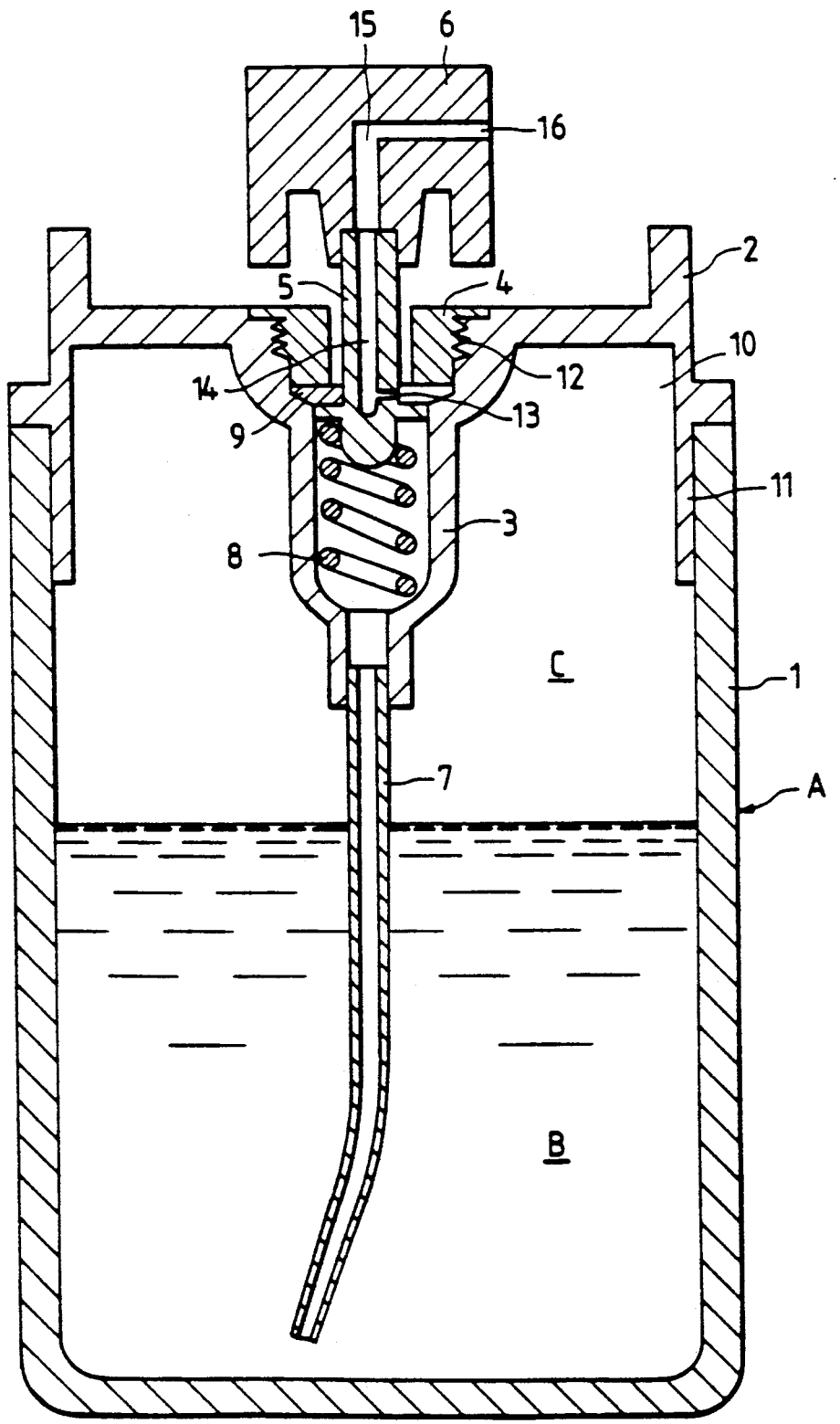
FIG. 4 is a longitudinal sectional view of one embodiment of the aerosol-type iodine microbicide composition of the present invention.

FIG. 4 is a sectional explanatory view of a spray device for the aerosol-type iodine microbicide composition of the present invention. In the drawing, (A) is an aerosol container, (B) is an iodine microbicide of the present invention, and (C) is a propellant. In the drawing, (1) is a tank body with an upper mouth (10), which contains the iodine microbicide (B) therein, and the shape of the longitudinal section thereof may be either circular or nearly rectangular. (2) is a mountain cap to shut the mouth (10) of the tank body (1), and this has a cylindrical part (11) having an outer diameter which almost corresponds to the inner diameter of the mouth (10) of the tank body (1). The cap (2) is fixed to the tank body (1) via the said cylindrical part (11). A housing (3) to house a spray device is disposed in the center of the mountain cap (2) towards the inside of the tank body (1), and the inner wall of the base edge of the said housing (3) has an internal thread so as to be engaged with the guide screw (4) which will be mentioned below. In the embodiment of FIG. 4, the mountain cap (2) and the housing (3) are integrated together, but these may be formed separately.

(5) is a stem, which has an inlet (13) for introducing the iodine microbicide (B) into the stem (5), in the side wall of the bottom. A duct (14) is provided in the inside of the stem (5), which passes therethrough from the inlet (13) to the upper end in the axial direction. The stem (5) has a jetting duct (15) as communicating with the duct (14), in the upper edge thereof, and the end of the jetting duct (15) has a push button (6) with a jetting nozzle (16). A spring (8) is disposed at the bottom of the stem (5), which is to return the stem (5) as pushed down for spraying to the natural state, the upper end of the spring (8) being contacted with the stem (5). (9) is a gasket having an action of preventing the leakage of the iodine microbicide (B) from the housing (3) and of opening and shutting the inlet (13) of the stem (5). (4) is a guide screw. After the above-mentioned gasket (9), spring (8) and stem (5) have been disposed in the determined positions, these are fixed by the action of the screw (4) by fastening this from the upper side thereof. The screw (4) has an external thread which may be engaged to the internal thread (12) as formed on the inner surface of the housing (3). The bottom of the housing (3) is connected with the top of a dip tube (7) the bottom of which is dipped in the iodine microbicide (B).

Among the above-mentioned constitutional members, those except the spring (8) and the gasket (9), or, that is, the tank body (1), the mountain cap (2), the housing (3), the guide screw (4), the stem (5), the push button (6) and the dip tube (7) are made of synthetic resins. In particular, since the tank body (1), the mountain cap (2), the housing (3), the guide screw (4) and the stem (5) are exposed to the iodine microbicide (B) at their inner wall and exposed to air at their outer wall, these members are made of synthetic resins which hardly permits iodine to permeate therethrough, for example, a polyacrylonitrile resin, a polyethylene terephthalate resin and a polyoxymethylene resin, so that iodine in the microbicide composition may not penetrate through the members from the inside to the outside. Although the spring (8) and the gasket (9) in this embodiment are not made of a synthetic resin, it is expected to use a so-called high function synthetic resin which is being developed in these days for forming these members. As a propellant for jetting the iodine there can be used one or more selected from Freon 11, Freon 12, liquefied petroleum gas, dimethyl ether and carbon dioxide gas.

The iodine microbicide-spraying device having the above-mentioned constitution is used for sterilization and disinfection of the surface of the intended objects, for example, as follows: The tank body (1) is caught with the hand, the push button (6) is pressed down so that the iodine microbicide (B) is jetted out from the nozzle (16). After the microbicide (B) has thus been applied to the surface of the object, for example, a stool, the microbicide (B) may be wiped with tissue paper or the like for the intended sterilization or disinfection.

The objects to which the iodine microbicide composition of the present invention is applied are not limited to only stools but the composition may also be used for sterilization or disinfection of a garbage receiver to be set at the corner of a sink.

In the iodine microbicide spraying device for the aerosol-type iodine microbicide composition of the present invention, since the main parts of the aerosol container to house the iodine microbicide are made of synthetic resins and, in particular, the tank body (1), the mountain cap (2), the housing (3) and the stem (5) are made of synthetic resins having a small gas-permeability to iodine, the active ingredient of the microbicide does not diffuse out from the container and the microbicidal effect of the composition in the container can be maintained for a long period of time. In addition, since the main parts of the device (container) of the present invention are made of synthetic resins, the weight of the container may be light and the container is conveniently portable. In the embodiment illustrated herein, since the mountain cap (2) and the housing (3) are integrally shaped, the number of the constitutional members may be reduced and the construction of the container from the respective parts is easy. Further, the air-tightness of the aerosol container may be improved and, as a result, the leakage of the propellant from the container may be inhibited and almost all of the iodine microbicide put in the container may be exhausted out without leaving some in the container.

Alternatively, the iodine microbicide composition of the present invention can be housed directly in a pump container to give a pump spray product, or a nonwoven fabric, paper, cloth or the like may be soaked with the composition to give a duster-type product, both in a conventional manner. The aerosol spray product and pump spray product containing the microbicidal composition of the present invention are not required to be diluted in use, which is different from the conventional microbicidal products. These can conveniently be used merely by pushing the push button of the container. In the case of the duster-type product, the amount of the iodine microbicide composition to be applied to the cloth or the like substrate may not be so high, which is also different from the conventional products. Accordingly, neither the article as disinfected with the duster-type product nor the hands for handling the same is discolored or roughened. Additionally, the product is almost free from any offensive odor. Thus the product of the present invention can be used with ease. The iodine microbicide composition of the present invention can be utilized in a broad range, for example, for disinfection of a stool as well as for disinfection of a sink and a garbage receiver to be disposed at the corner of a sink.

The present invention will be explained in greater detail by way of the following examples and comparative examples, which, however, are not intended to restrict the scope of the present invention.

EXAMPLES 1 TO 6 AND COMPARATIVE EXAMPLES 1 TO 4

Various kinds of iodine microbicide compositions each having the components as shown in Table 1 below were prepared by a conventional method, and the stability of the respective compositions as well as the feeling in actual use of the compositions were evaluated in the manners as mentioned below.

Stability

The effective iodine concentration of each of the thus prepared iodine microbicide compositions was measured by a conventional method, at the starting of the test (initial value) and after storage under an atmosphere of 40° C. for 6 months. Next, the effective iodine retentivity was calculated from the following formula:

$$\text{Effective Iodine Retentivity (\%)} = \frac{\text{Effective Iodine Concentration of Sample After Storage for 6 Months}}{\text{Effective Iodine Concentration at the Starting of the Test}} \times 100$$

The stability was evaluated on the basis of the following criteria:
O: Effective iodine retentivity was 80% or more.
X: Effective iodine retentivity was less than 80%.

Feeling in Actual Use

The color and odor as become more positive with increase of the iodine concentration in the iodine microbicide composition were evaluated on the basis of the following criteria:
O: There was no psychological resistance to the practical use of the composition.
X: There was some psychological resistance to the practical use of the composition.

Total Evaluation

Summarizing the above-mentioned evaluations, the total evaluation was made on the basis of the following criteria:
O: There was no problem on both the stability and the feeling in the actual use.
X: There was at least one problem on either or both of the stability and the feeling in the actual use. The results obtained are shown in Table 1 below.

TABLE 1

|  | Examples |  |  |  |  |  | Comparative Examples |  |  |  |
|---|---|---|---|---|---|---|---|---|---|---|
|  | 1 | 2 | 3 | 4 | 5 | 6 | 1 | 2 | 3 | 4 |
| Components (wt. %) |  |  |  |  |  |  |  |  |  |  |
| Ethanol (99.5%) | 99.99 | 94.95 | 80.0 | 99.8 | 99.9995 | 99.0 | 94.9 | 89.9 | 99.9999 | 98.9 |
| Ethylene Glycol (99.9%) | — | 5 | 19.9 | — | — | — | — | 5 | — | — |
| Povidone-Iodine | 0.01 | 0.05 | 0.1 | 0.2 | 0.0005 | 1.0 | 0.1 | 0.1 | 0.0001 | 1.1 |
| Pure Water | — | — | — | — | — | — | 5 | 5 | — | — |
| Evaluation |  |  |  |  |  |  |  |  |  |  |
| Stability | O | O | O | O | O | O | X | X | X | O |
| Feeling in Actual Use | O | O | O | O | O | O | O | O | O | X |
| Total Evaluation | O | O | O | O | O | O | X | X | X | X |

As is obvious from the results in Table 1, the iodine microbicide compositions were excellent in both the stability and the feeling in the actual use only when the content of the povidone-iodine therein was from 0.0005% to 1.0% by weight to the total weight of the composition and the compositions were substantially non-aqueous.

EXAMPLE 7 AND COMPARATIVE EXAMPLES 5 AND 6

Iodine microbicide compositions were prepared by a conventional method, each having the components mentioned in Table 2 below. The stability test of the respective compositions was carried out, as mentioned below.

Stability Test

Figure 2:
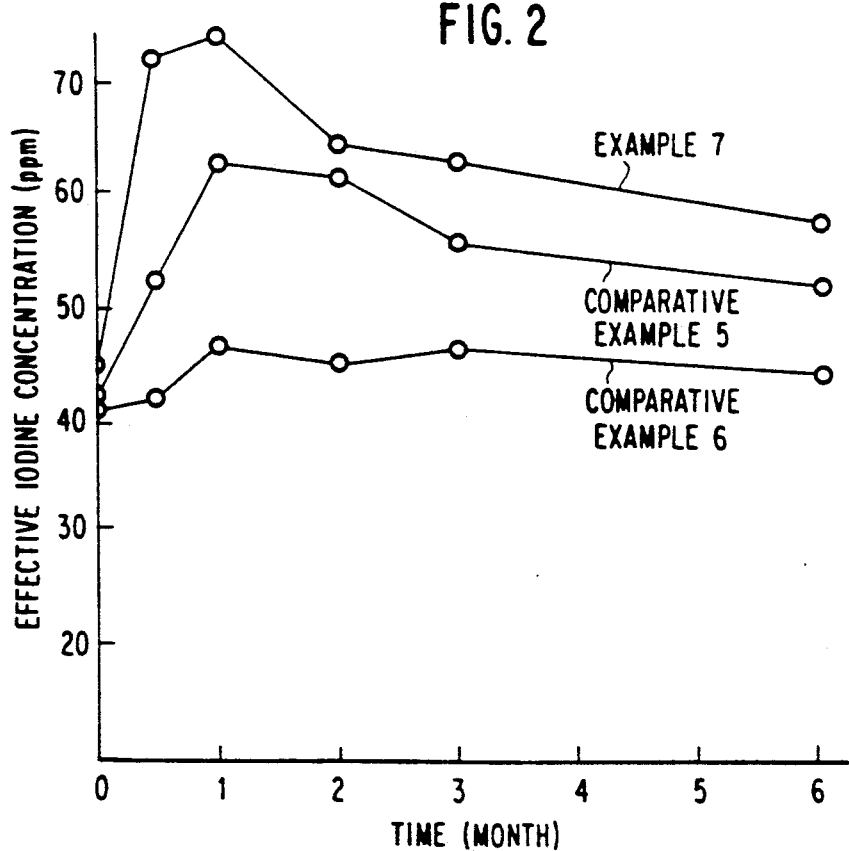
FIG. 2 is a graph showing the time-dependent change of the effective iodine concentration in the iodine microbicide compositions prepared in Example 7 and Comparative Examples 5 and 6 each having a different ethanol concentration, which were stored under the condition of room temperature.
Figure 3:
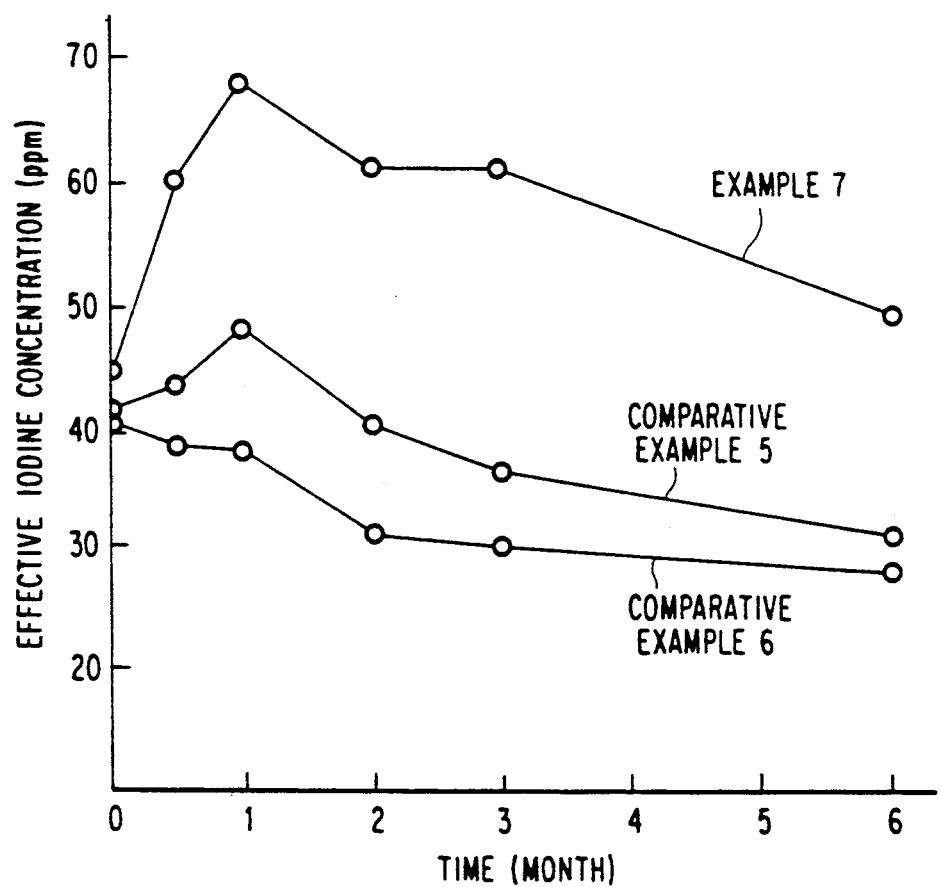
FIG. 3 is a graph showing the time-dependent change of the effective iodine concentration in the iodine microbicide compositions prepared in Example 7 and Comparative Examples 5 and 6 each having a different ethanol concentration, which were stored under the condition of 40° C.

The effective iodine concentration of the respective iodine microbicide compositions prepared was measured by a conventional method, at the start of the test and after storage for 0.5, 1, 2, 3 and 6 months at −5° C., room temperature or 40° C. The results obtained are shown in Table 2 below and in FIGS. 1 to 3 attached hereto. In FIGS. 1 to 3, the axis of the abscissa means the effective iodine concentration (ppm) and the axis of the ordinate means the time (month).

TABLE 2

|  |  | Comparative Example |  |
|---|---|---|---|
|  | Example 7 | 5 | 6 |
| Components (wt. %) |  |  |  |
| Ethanol (99.5%) | 99.95 | 94.95 | 89.95 |
| Water | — | 5.00 | 10.00 |
| Povidone-Iodine | 0.05 | 0.05 | 0.05 |
| Effective Iodine Concentration (ppm) |  |  |  |
| At the Start of Test (Control) | 44 | 41 | 40 |
| After Storage for 3 Months |  |  |  |
| −5° C. | 56 | 40 | 38 |
| Room Temperature | 62 | 55 | 47 |
| 40° C. | 61 | 36 | 30 |
| After Storage for 6 Months |  |  |  |
| −5° C. | 56 | 40 | 38 |
| Room Temperature | 57 | 52 | 44 |
| 40° C. | 49 | 31 | 28 |

As is obvious from the results in Table 2 and in FIGS. 1 to 3, the effective iodine concentration was higher when the ethanol concentration was higher and the temperature is nearer to room temperature. Although the effective iodine concentration fluctuated, as starting from the initial value of from 40 to 44 ppm, with the lapse of time, the effective iodine retentivity in the sample of Example 7 was found to be 80% or more of the initial value at least within the temperature condition of from −5° C. to 40° C. even after storage for 6 months.

EXAMPLES 8 AND 9 AND COMPARATIVE EXAMPLES 7 TO 12

An iodine microbicide composition comprising 99.95% by weight of ethanol and 0.05% by weight of povidone-iodine was blended with a propellant comprising 60% by weight of Freon 11 and 40% by weight of Freon 12 in a weight ratio of 3/7, and then the resulting mixture was put in an aerosol container made of the materials shown in Table 3 below. The effective iodine stability of the thus prepared aerosol-type iodine microbicide compositions and the corrosion-resistance of the inner wall of the containers were evaluated, as mentioned below.

Effective Iodine Stability

The effective iodine concentration of each of the aerosol-type iodine microbicide compositions prepared above was measured, at the start of the test and after storage for 6 months under an atmosphere of 45° C., by a conventional method, and the effective iodine retentivity was calculated from the data obtained, in the same manner as mentioned above. The evaluation was based upon the following criteria:

O: Effective iodine retentivity was 80% or more.

X: Effective iodine Retentivity was less than 80%.

Corrosion-Resistance of Inner Wall of Container

Each of the aerosol-type iodine microbicide compositions prepared above was stored for 6 months under an atmosphere of 45° C., and the morphologic change of whitening, swelling, peeling, rusting or the like, if any, on the surface of the inner wall of the container was observed. The evaluation was based upon the following criteria:

O: No morphologic change was found.

X: Morphologic change was found.

Total Evaluation

Summarizing the above-mentioned evaluations, the total evaluation was made on the basis of the following criteria:

O: There was no problem on both the effective iodine stability and the corrosion-resistance of the inner wall of the container.

X: There was at least one problem on either or both of the effective iodine stability and the corrosion-resistance of the inner wall of the container. The results are shown in Table 3 below.

TABLE 3

| | Example | | Comparative Example | | | | | |
|---|---|---|---|---|---|---|---|---|
| | 8 | 9 | 7 | 8 | 9 | 10 | 11 | 12 |
| Materials of Container | | | | | | | | |
| Tank Body | Polyacrylonitrile Resin | Polyethylene Terephthalate Resin | Epoxyurea resin-coated tin plate | Epoxyurea resin-coated aluminium | Epoxyphenol resin-coated tin plate | Epoxyphenol resin-coated aluminium | Micoflex-coated tin plate | Micoflex-coated aluminium |
| Mountain Cap | Polyacrylonitrile Resin | Polyethylene Terephthalate Resin | Epoxyurea resin-coated tin plate | Epoxyurea resin-coated aluminium | Epoxyphenol resin-coated tin plate | Epoxyphenol resin-coated aluminium | Micoflex-coated tin plate | Micoflex-coated aluminium |
| Housing | Polyacrylonitrile Resin | Polyethylene Terephthalate Resin | Nylon | Nylon | Nylon | Nylon | Nylon | Nylon |
| Stem | Polyoxymethylene Resin | Polyoxymethylene Resin | Nylon | Nylon | Nylon | Nylon | Nylon | Nylon |
| Effective Iodine Stability | O | O | X | X | X | X | X | X |
| Corrosion-Resistance of Inner Wall of Container | O | O | X | X | X | X | X | X |
| Total Evaluation | O | O | X | X | X | X | X | X |

As is obvious from the results in Table 3, when the iodine microbicide composition of the present invention was, together with a propellant, put in an aerosol container made of one or more synthetic resins selected from the group consisting of a polyacrylonitrile resin, polyethylene terephthalate resin and a polyoxyethylene resin, there was no remarkable change in both the composition and the container even after storage for 6 months under an atmosphere of 45° C. and in particular there was no morphologic change in the inner wall of the container. As opposed thereto, however, when the iodine microbicide composition of the present invention was, together with a propellant, put in a conventional tin or aluminium container whose inner surface had been coated with a conventional resin, the effective iodine concentration in the composition noticeably decreased and the inner wall of the container was noticeably corroded after storage for 6 months under an atmosphere of 45° C.

In the iodine microbicidal composition of the present invention, since the content of the povidone-iodine as dissolved in a substantially non-aqueous solvent comprising a lower alcohol having from 1 to 3 carbon atoms or a mixture of a lower alcohol having from 1 to 3 carbon atoms and a non-hydrated polyhydric alcohol is defined to fall within the range of from 0.0005 to 1.0% by weight to the total weight of the composition, the microbicidal activity of the iodine composition may be elevated and the iodine concentration in the composition may be stably maintained. Accordingly, the present invention provides an iodine microbicidal composition whose microbicidal activity is not lowered even after storage for a long period of time. In particular, since alcohols themselves have a microbicidal activity, the microbicidal activity of the composition of the present invention is really far more excellent than the conventional aqueous solution-type iodine microbicide compositions. In addition, since the iodine concentration in the composition of the present invention is low, there is no problem of coloration of the objects to which the composition is applied, even when the composition is adhered to the objects, or of the iodine-specific offensive odor. Accordingly, the iodine microbicide composition of the present invention can actually be used with ease.

Further, since the aerosol-type microbicide composition is housed in the container comprising the constitutional parts mentioned above, the weight is light and the container is handy to carry. For actual use, the push button may only be pushed to spray out the iodine microbicide from the container to the intended objects, and the composition is not required to be diluted in use. The handling of the aerosol-type container of the present invention is thus very easy and simple. In the aerosol container of the spraying device of the present invention, at least the tank body, the mountain cap, the housing and the stem are made of synthetic resins having a small gas-permeability to iodine and metal parts which will react with iodine are used almost nowhere. Accordingly, the iodine microbicide contained in the container does not react with the container to deteriorate, or the active ingredient does not diffuse out through the container Thus the microbicidal activity of the iodine microbicide composition of the present invention can be maintained for a long period of time.

While the invention has been described in detail and with reference to specific embodiments thereof, it will be apparent to one skilled in the art that various changes and modifications can be made therein without departing from the sprit and scope thereof.

What is claimed is:

1. An aerosol iodine microbicide composition comprising an aerosol container having contained therein a substantially non-aqueous iodine microbicide composition and a propellant, said aerosol container comprising a tank body, a mountain cap, a housing and a stem which are made of one or more synthetic resins selected from the group consisting of a polyacrylonitrile resin, a polyethylene terephthalate resin and a polyoxymethylene resin, wherein said substantially non-aqueous iodine microbicide composition comprises
   (a) a povidone-iodine in an amount of from 0.0005% to 1.0% by weight based on the total amount of said composition, and
   (b) a solvent comprising a lower alcohol having from 1 to 3 carbon atoms or a mixture of a lower alcohol having from 1 to 3 carbon atoms and a non-hydrated polyhydric alcohol,
   wherein the amount of said lower alcohol is 80% by weight or more based on the total weight of said composition.

2. An aerosol iodine microbicide composition comprising an aerosol container having contained therein the substantially non-aqueous iodine microbicide composition of claim 1, wherein the amount of said povidone-iodine is from 0.01% to 0.5% by weight based on the total weight of said composition.

3. An aerosol iodine microbicide composition comprising an aerosol container having contained therein the substantially non-aqueous iodine microbicide composition of claim 1, wherein said solvent comprises said lower alcohol having from 1 to 3 carbon atoms.

4. An aerosol iodine microbicide composition comprising an aerosol container having contained therein the substantially non-aqueous iodine microbicide composition of claim 1, wherein said lower alcohol having from 1 to 3 carbon atoms is ethanol.

* * * * *